(12) United States Patent
Kuhn

(10) Patent No.: US 6,624,330 B2
(45) Date of Patent: Sep. 23, 2003

(54) METHOD FOR STABILIZING PHENYLACETALDEHYDE

(75) Inventor: Walter Kuhn, Holzminden (DE)

(73) Assignee: Haarmann & Reimer GmbH (DE)

( * ) Notice: Subject to any disclaimer, the term of this patent is extended or adjusted under 35 U.S.C. 154(b) by 0 days.

(21) Appl. No.: 10/005,007

(22) Filed: Dec. 4, 2001

(65) Prior Publication Data

US 2002/0128518 A1 Sep. 12, 2002

(30) Foreign Application Priority Data

Dec. 7, 2000 (DE) .......................... 100 60 755

(51) Int. Cl.$^7$ .............................. C07C 47/09
(52) U.S. Cl. ...................... 568/421; 568/426; 568/435; 568/438; 568/441
(58) Field of Search ................ 568/426, 435, 568/438, 441, 421

(56) References Cited

U.S. PATENT DOCUMENTS

| | | | |
|---|---|---|---|
| 2,280,311 A | 4/1942 | Roblin, Jr. .................. | 260/599 |
| 4,414,419 A | 11/1983 | Weber et al. ................ | 568/421 |
| 6,137,013 A | 10/2000 | Riedel et al. ............... | 568/421 |
| 6,150,563 A | 11/2000 | Hasselbach et al. ......... | 568/422 |

FOREIGN PATENT DOCUMENTS

| DE | 29 05 267 | 7/1980 |
|---|---|---|
| SU | 1705273 | 1/1992 |

OTHER PUBLICATIONS

70012282, Derwent Japan (Abstract only attached).

Steffen Arctander, Perfume and Flavor Chemicals, Monclair, N.J. USA, (month unavailable) 1969, No. 2470, Phenylactaldehyde.

Kurt Bauer, Dorothea Garbe, Horst Surburg, Common Fragrance and Flavor Materials, VCH Weinheim, (month unavailable) 1985, p. 68, Single Fragrance and Flavor Compounds.

*Primary Examiner*—Johann Richter
*Assistant Examiner*—SiKarl A. Witherspoon
(74) *Attorney, Agent, or Firm*—Pendorf & Cutliff

(57) ABSTRACT

The present invention relates to a method for stabilizing phenylacetaldehyde by adding at least one additive, in which case the additive contains one or more polybasic carboxylic acids.

9 Claims, No Drawings

METHOD FOR STABILIZING PHENYLACETALDEHYDE

FIELD OF THE INVENTION

The present invention relates to a method for stabilizing phenylacetaldehyde against polymerization and autocondensation.

BACKGROUND OF THE INVENTION

Phenylacetaldehyde occurs in essential oils and is a volatile constituent of foods. Its odor resembles hyacinth. Phenylacetaldehyde can be prepared by a rearrangement of styrene oxide and is used in fragrance compositions and flavorings; K. Bauer, A. Garbe, Common Fragrance and Flavor Materials, p. 68, VCH, Weinheim, 1985; S. Steffen Arctander, Perfume and Flavor Chemicals, No. 2470, Montclair, N.J., USA 1969.

Phenylacetaldehyde, owing to its high reactivity, has a tendency towards polymerization and autocondensation. In polymerization, predominantly 2,4,6-tribenzyl-1,3,5-trioxane forms. Trimerization is catalyzed by the presence of chemical substances such as chlorine or bromine, phosphorus pentoxide, sulfuric acid, hydrogen sulphide, hydrogen chloride, hydrogen fluoride, boron trifluoride, aluminum chloride, iron chloride or zinc chloride. In the presence of acidic compounds, the polymerization of phenylacetaldehyde begins spontaneously. Furthermore, low temperatures from about 0° C., or UV light, promote polymerization.

A further problem is the tendency of phenylacetaldehyde to be subjected to aldol condensation in the presence of alkaline substances.

It is known that the polymerization and autocondensation reactions of aldehydes can be prevented by the addition of certain substances. In the processing and use of phenylacetaldehyde as a fragrance and flavoring, the added chemical substances must not interfere organoleptically and must be permissible under food legislation.

DE-A 29 05 267 and DE-A 29 17 789 disclose that aliphatic aldehydes can be stabilized against polymerization and autocondensation by adding triethanolamine or dimethylethanolamine. However, a disadvantage of these stabilizers is that they are undesirable in foods and can only be removed again from the aldehydes by complex distillation.

JP 45 012282 B4 and DE A 19757531 describe the stabilization of aliphatic aldehydes by alkali metal hydroxides, alkaline earth metal hydroxides, alkali metal carbonates, alkaline earth metal carbonates or alkaline earth metal carboxylates. A disadvantage of this method is that the substances added do not dissolve and disperse completely. A uniform distribution of the alkaline substance in the entire volume of aldehyde is difficult to achieve.

SU A 1705273 describes the stabilization of phenylacetaldehyde by combining three classes of substances; i.e.

1. a free-radical scavenger such as alpha-tocopherol or butylated hydroxyanisole
2. a diphenylamine derivative such as dimethylbis(p-phenylaminophenoxy)silane and
3. a hydroxy acid such as tartaric acid, ascorbic acid or citric acid.

A disadvantage of this method is the extensive usage of substances. In addition, the diphenylamine derivatives described are not permitted in foods.

SUMMARY OF THE INVENTION

Therefore, it is an object of the present invention to provide a method for stabilizing phenylacetaldehyde by adding one or more additives, which method does not have the abovementioned disadvantages.

A method has been found for stabilizing phenylacetaldehyde by adding one or more additives wherein the additives contain one or more polybasic carboxylic acids.

DETAILED DESCRIPTION OF THE INVENTION

According to the present invention, the polybasic carboxylic acids are used in amounts of 10 to 1,000 ppm. Preference is given to 100 to 300 ppm.

Polybasic carboxylic acids, which come into consideration are in particular, oxalic acid, malonic acid, succinic acid, glutaric acid, adipic acid, pimelic acid, suberic acid, citric acid, maleic acid or fumaric acid.

The carboxylic acids, which come into consideration, are harmless in the food sector. Therefore, it is no longer necessary to remove unwanted substances with considerable effort. It is also advantageous that the carboxylic acids described are completely soluble and dispersible. This ensures even distribution in the volume of aldehyde. The consequence is optimum stabilization of the phenylacetaldehydes present. It is surprising that addition of polybasic carboxylic acids alone, that is to say without using other additives, achieves the advantages described. The inventive method is, thus, also very simple and inexpensive.

The present invention relates to an additive-containing phenylacetaldehyde. This additive is characterized in that it contains one or more polybasic carboxylic acids.

In addition, the present invention relates to the use of the stabilized phenylacetaldehyde for preparing fragrance compositions and flavorings.

EXAMPLES

Example 1

200 ppm of oxalic acid or 200 ppm of citric acid were added to freshly distilled phenylacetaldehyde. These samples were stored at 20° C. and 40° C. The reduction in phenylacetaldehyde content was followed using the carbonyl value:

|  | Carbonyl value at 20° C. after 28 days |
| --- | --- |
| Phenylacetaldehyde with no addition | 93.2% |
| Phenylacetaldehyde with citric acid | 99.2% |
| Phenylacetaldehyde with oxalic acid | 99.4% |

|  | Carbonyl value at 40° C. after 28 days |
| --- | --- |
| Phenylacetaldehyde with no addition | 81.9% |
| Phenylacetaldehyde with citric acid | 97.0% |
| Phenylacetaldehyde with oxalic acid | 98.3% |

The inventive method can be carried out by introducing the stabilizer and adding phenylacetaldehyde, or adding phenylacetaldehyde to the stabilizer. Stirring is not necessary.

Example 2

Alpha-tocopherol is a natural antioxidant that is used in the food sector.

|  | Carbonyl value at 20 degrees C. after 42 days |
|---|---|
| Phenylacetaldehyde with no addition | 82.5% |
| Phenylacetaldehyde with 100 ppm citric acid | 99.3% |
| Phenylacetaldehyde with 100 ppm alpha-tocopherol | 86.8% |
| Phenylacetaldehyde with 300 ppm alpha-tocopherol | 86.4% |
| Phenylacetaldehyde with 500 ppm alpha-tocopherol | 87.0% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for stabilizing phenylacetaldehyde by adding one or more additives, wherein said additives consist essentially of one or more polybasic carboxylic acids.

2. A method for stabilizing phenylacetaldehyde by adding one or more additives, wherein said additives consist of one or more polybasic carboxylic acids.

3. A method according to claim 1, wherein the polybasic carboxylic acid is added in amounts of 100 to 300 ppm.

4. A method according to claim 1, wherein said polybasic carboxylic acid is first introduced and then followed by the addition of phenylacetaldehyde.

5. A method according to claim 1, wherein said polybasic carboxylic acid is added to the phenylacetaldehyde.

6. A method according to claim 2, wherein the polybasic carboxylic acid is added in amounts of 100 to 300 ppm.

7. A method according to claim 2, wherein said polybasic carboxylic acid is first introduced and then followed by the addition of phenylacetaldehyde.

8. A method according to claim 2, wherein said polybasic carboxylic acid is added to the phenylacetaldehyde.

9. A process for the preparation of fragrance or flavor compositions comprising the stabilization of phenylacetaldehyde by adding one or more polybasic carboxylic acids, wherein the polybasic carboxylic acid is added in amounts of 10 to 1000 ppm and wherein said polybasic carboxylic acid is selected from the group consisting of oxalic acid, malonic acid, succinic acid, glutaric acid, adipic acid, pimelic acid, suberic acid, citric acid, maleic acid, fumaric acid, and combinations of these acids.

* * * * *